(12) United States Patent
Maschke

(10) Patent No.: US 7,686,767 B2
(45) Date of Patent: *Mar. 30, 2010

(54) CATHETER WITH VARIABLE MAGNETIC FIELD GENERATOR FOR CATHETER GUIDANCE IN A SUBJECT

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 621 days.

This patent is subject to a terminal disclaimer.

(21) Appl. No.: 10/353,883

(22) Filed: Jan. 29, 2003

(65) Prior Publication Data

US 2003/0176786 A1    Sep. 18, 2003

(30) Foreign Application Priority Data

Jan. 29, 2002    (DE)    ............... 102 03 371

(51) Int. Cl.
*A61B 6/00* (2006.01)
*A61B 8/00* (2006.01)

(52) U.S. Cl. ...................... 600/466; 600/435

(58) Field of Classification Search ......... 600/422–425, 600/434, 435, 462, 466, 467, 411, 409; 606/108, 606/130; 604/528, 282, 264
See application file for complete search history.

(56) References Cited

U.S. PATENT DOCUMENTS

| | | | | |
|---|---|---|---|---|
| 4,134,405 A * | 1/1979 | Smit | ......................... | 606/108 |
| 4,175,566 A * | 11/1979 | Millar | ......................... | 600/505 |
| 4,821,731 A * | 4/1989 | Martinelli et al. | ........... | 600/463 |
| 5,125,888 A * | 6/1992 | Howard et al. | ................ | 600/12 |
| 5,211,165 A * | 5/1993 | Dumoulin et al. | ........... | 600/410 |
| 5,243,988 A * | 9/1993 | Sieben et al. | ............... | 600/463 |
| 5,269,759 A * | 12/1993 | Hernandez et al. | ........ | 604/96.01 |
| 5,334,207 A * | 8/1994 | Gay, Jr. | ......................... | 606/7 |
| 5,353,795 A * | 10/1994 | Souza et al. | ................ | 600/423 |
| 5,425,367 A * | 6/1995 | Shapiro et al. | ............... | 600/424 |
| 5,431,640 A * | 7/1995 | Gabriel | ....................... | 604/270 |
| 5,509,044 A * | 4/1996 | Horbaschek | ................ | 378/97 |
| 5,542,938 A * | 8/1996 | Avellanet et al. | ............ | 604/528 |
| 5,572,132 A * | 11/1996 | Pulyer et al. | ................ | 324/318 |
| 5,630,427 A * | 5/1997 | Hastings | ..................... | 604/524 |
| 5,706,827 A * | 1/1998 | Ehr et al. | .................... | 600/585 |
| 5,729,129 A * | 3/1998 | Acker | .................... | 324/207.12 |
| 5,813,996 A * | 9/1998 | St. Germain et al. | ........ | 600/585 |
| 6,126,647 A * | 10/2000 | Posey et al. | ................. | 604/270 |
| 6,148,823 A | 11/2000 | Hastings | | |
| 6,173,199 B1 * | 1/2001 | Gabriel | ....................... | 600/424 |
| 6,216,026 B1 * | 4/2001 | Kuhn et al. | ................. | 600/409 |
| 6,233,474 B1 * | 5/2001 | Lemelson | ................... | 600/411 |
| 6,280,385 B1 * | 8/2001 | Melzer et al. | ............... | 600/423 |
| 6,298,261 B1 | 10/2001 | Rex | | |

(Continued)

FOREIGN PATENT DOCUMENTS

DE    40 37 586    5/1992

(Continued)

*Primary Examiner*—Eric F Winakur
*Assistant Examiner*—Lawrence N Laryea
(74) *Attorney, Agent, or Firm*—Schiff Hardin LLP

(57) ABSTRACT

A catheter, particularly an intra-vascular catheter, has at least one magnetic field-generating element arranged in the catheter envelope in the region of the catheter tip, characterized in that the magnetic field of which is variable while the catheter is inserted into a patient.

10 Claims, 4 Drawing Sheets

U.S. PATENT DOCUMENTS

| | | | |
|---|---|---|---|
| 6,311,082 B1 * | 10/2001 | Creighton et al. | 600/407 |
| 6,317,091 B1 | 11/2001 | Oppelt | |
| 6,321,109 B2 * | 11/2001 | Ben-Haim et al. | 600/424 |
| 6,332,089 B1 * | 12/2001 | Acker et al. | 600/424 |
| 6,385,472 B1 * | 5/2002 | Hall et al. | 600/374 |
| 6,408,202 B1 * | 6/2002 | Lima et al. | 600/423 |
| 6,487,437 B1 * | 11/2002 | Viswanathan et al. | 600/423 |
| 6,505,062 B1 * | 1/2003 | Ritter et al. | 600/407 |
| 6,507,751 B2 * | 1/2003 | Blume et al. | 600/424 |
| 6,522,909 B1 * | 2/2003 | Garibaldi et al. | 600/424 |
| 6,524,303 B1 * | 2/2003 | Garibaldi | 604/525 |
| 6,690,963 B2 * | 2/2004 | Ben-Haim et al. | 600/424 |
| 6,704,594 B1 * | 3/2004 | Blank et al. | 600/423 |
| 6,724,290 B1 * | 4/2004 | Ohnmacht et al. | 336/200 |
| 2002/0103430 A1 * | 8/2002 | Hastings et al. | 600/411 |
| 2003/0135111 A1 * | 7/2003 | Meaney et al. | 600/422 |
| 2003/0160721 A1 * | 8/2003 | Gilboa et al. | 342/450 |
| 2004/0236344 A1 * | 11/2004 | Monstadt et al. | 606/108 |

FOREIGN PATENT DOCUMENTS

| | | |
|---|---|---|
| DE | 42 15 901 | 8/1993 |
| DE | 196 29 890 | 4/1997 |
| DE | 198 35 658 | 2/2000 |
| GB | 2 313 668 | 12/1997 |

\* cited by examiner

Electro magnets

CATHETER WITH VARIABLE MAGNETIC FIELD GENERATOR FOR CATHETER GUIDANCE IN A SUBJECT

BACKGROUND OF THE INVENTION

1. Field of the Invention

The present invention is directed to a catheter, particularly an intra-vascular catheter, having at least one magnetic field-generating element arranged in the catheter envelope in the region of the catheter tip.

2. Description of the Prior Art

A catheter is an elongated instrument that, for example, is inserted into a vessel track of the human or animal body up to a certain point. For example, such catheters are utilized in the framework of treating diseases of the arterial coronary vessels that cause a cardiac infarction. In the case of arteriosclerosis, deposits (arteriosclerotic plaque) occur at the vessel wall and thus lead to a "plugging" of one or more coronary vessels. By employment of a catheter, the diseased vessel regions can be reached and treatment activity can be undertaken.

For moving and guiding the catheter inserted into the vessel, it is known to employ an externally generated magnetic field with which the magnetic field of a permanent magnet arranged in the region of the catheter tip interacts. For example, U.S. Pat. No. 6,148,823 discloses such a system. It is necessary to vary the external magnetic field for moving the catheter. This ensues in the known system using a C-like device to generate the external magnetic field that is arranged so as to be movable at the floor side. The open ends of the C-like device are arranged above and below the patient, so that the device can be displaced relative to the patient. A disadvantage, however, is that this field-generating device is very heavy and is thus somewhat difficult to move. Difficulties arise due the cumbersome nature of the device particularly when the catheter is to be moved around a vessel bend, where it encounters greater resistance and is prone to become lodged. A further disadvantage is that, due to the employment of a permanent magnet in the catheter, the magnetic coupling between its magnetic field and the external magnetic field may not be strong enough in order to overcome the aforementioned resistance, for example because the external magnetic field is somewhat attenuated in the region where the magnetic tip of the catheter is located.

German OS 40 37 586 discloses a medical probe for examining a body that emits electromagnetic waves that are acquired by a receiver arranged outside the body, allowing the probe can be localized. For example, this can then be presented in an X-ray image.

U.S. Pat. No. 6,298,261 discloses a catheter tracking system. A number of transducers are utilized as locating aids, one of which is arranged on the head of the catheter.

German OS 42 15 901 discloses a catheter having a localizable end region for locating the catheter or the catheter tip.

German OS 198 35 658 discloses a method for localizing an MR endoscope wherein rapidly changing magnetic fields at 10-200 Hz or 1 through 120 MHz are utilized in order to determine the position of a probe. This particularly serves the purpose of avoiding direct current and the forces generated therewith.

U.S. Pat. No. 6,317,091 discloses an apparatus for inductively coupling a magnetic resonance signal into a reception antenna as well as a medical intervention instrument.

U.S. Pat. No. 6,280,385 discloses an MR imaging method for the presentation, position identification or functional control of a device introduced into an examination subject, as well as an apparatus for employment in such a method that has various coil arrangements for locating or displaying the catheter tip.

German OS 196 29 890 discloses magnetic resonance devices suitable for re-adjustment as well as imaging for the locating and position determination of a catheter and, additionally, for MR imaging.

British Specification 2 313 668 discloses a sampling ultrasound probe with locally driven wobble ultrasound source for generating ultrasound images.

These systems only serve the purpose of locating a catheter. The aforementioned problems in the manual movement of the catheter by a physician thus continue to exist. The physician is also not provided with any further information by these locating systems.

SUMMARY OF THE INVENTION

An object of the present invention is to provide a catheter that alleviates the aforementioned problems.

The object is achieved in accordance with the invention in a catheter of the type initially described wherein the magnetic field is variable while the catheter is inserted into a patient.

The magnetic field generated at the catheter is not fixed or unalterable, but can be varied in terms of field strength or field direction as needed. This creates the possibility, for example, of increasing the field strength as needed, so that the above-cited problems as to a non-optimum coupling to the external field can be overcome. Moreover, there is the possibility of varying the field direction. It is possible to vary the field direction, as needed, of not only the external field but also the field of the inner magnetic element. As a result, it is possible by means of designated variation of the catheter's magnetic field and a designated variation of the external magnetic field to influence the interaction of the two and thus to be able to utilize and vary the coupling effect on the catheter tip that arises from the interaction of the two fields, and is expressed in directed interaction forces on the catheter tip. As a result, differently directed forces can be exerted on the catheter tip. This enables a simpler navigation and movement of the catheter in the patient.

In order to be able to vary the catheter's magnet field in a simple way, an electromagnet with a core and a coil is expediently utilized as the magnetic field-generating element. The leads of the coil are guided in the catheter envelope and can be supplied with current from outside the patient. Magnetic fields that differ in size and/or direction can be generated dependent on how high the coil current is and the direction the current is conducted through the coil. Expediently, two or more electromagnets can be provided that can be driven individually or together. As a result, it is possible—for example by field superimposition—to generate even stronger fields than with a single electromagnet.

In an embodiment of the invention, (at least one) electromagnet is arranged such that the magnetic field that can be generated resides essentially parallel to the longitudinal axis of the catheter. In this embodiment, thus, the coil is wound around the longitudinal axis of the catheter; the middle of the coil coincides with the longitudinal axis. The magnetic field that can be generated lies in the axial direction; its direction is dependent on the coil current.

In comparison thereto, in an alternative electromagnet arrangement the magnet field that can be generated resides essentially perpendicularly to the longitudinal axis of the catheter. In this case, the coil winding lies in the direction of the longitudinal axis of the catheter, so that an orthogonal magnetic field can be generated.

In a further embodiment of the invention at least two electromagnets are arranged such that their respective magnetic fields reside essentially orthogonally relative to one another, i.e. one magnetic field lies essentially parallel to the longitudinal axis and the other lies essentially perpendicular thereto. In this embodiment of the invention, it is possible to generate either discretely directed fields or—by superimposition, i.e. operation of both electromagnets—to generate a resultant overall field that resides at an angle relative to the directions of the component magnetic fields.

At least one permanent magnetic element can be provided in the region of the catheter tip. This will suffice in many cases for the movement of the catheter with the external magnetic field, so that it is only necessary to supply the electromagnet or electromagnets with current when required.

It is expedient to provide an ultrasound generating and image pickup device is provided in the region of the catheter tip, so the catheter includes not only the magnetic motion and guidance device in the tip but also the image generating and pickup device. Employment of the magnetic guidance and positioning system, offers the possibility of being able to position and navigate the catheter exactly in view of the diseased body region as well as being able to make ultrasound images thereof. X-ray monitoring, as is conventionally employed, does not allow an image presentation of the vessel wall but only of the vessel volume. The augmentation of monitoring with evaluation of the ultrasound images, allows the vessel wall itself to be seen.

DESCRIPTION OF THE PREFERRED EMBODIMENTS

Figure 1:
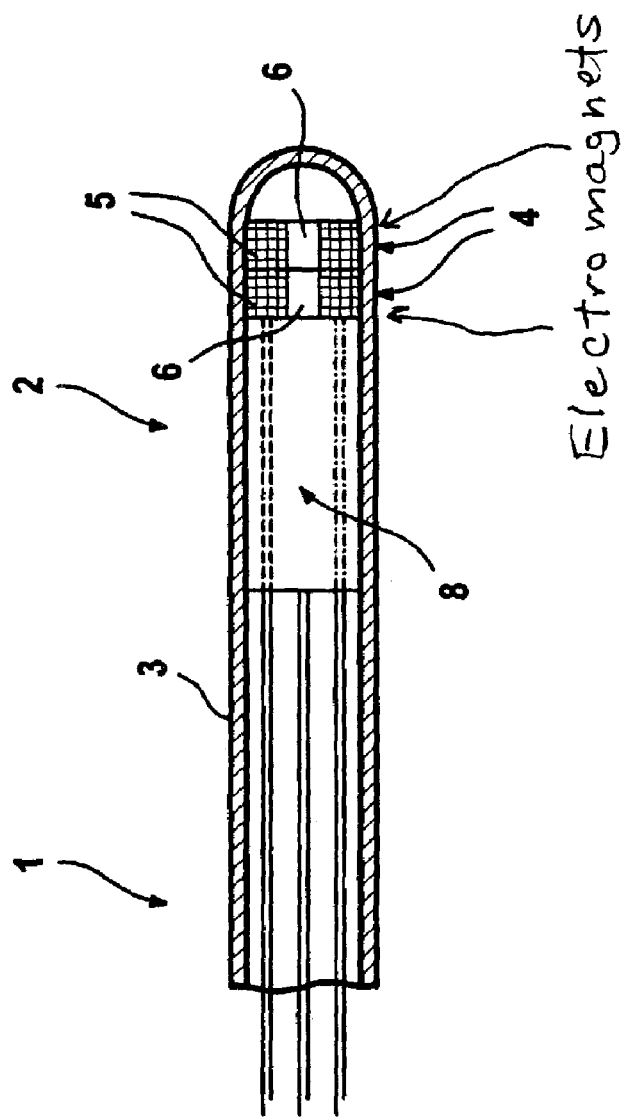
FIG. 1 is a schematic sectional illustration of the inventive catheter in a first embodiment.

FIG. 1 shows the inventive catheter 1 with a tip 2 at which two electromagnets 4 are positioned at fixed locations in the inside of the catheter envelope 3 in the illustrated example. Each electromagnet 4 is composed of a coil 5 and a core 6, for example an iron core. Separate leads 7 are provided in the inside of the catheter envelope, these being conducted toward the outside. The respective coils 5 of the electromagnets 4 are able to be separately supplied with current via the leads 7.

An ultrasound system 8 for generating ultrasound and for picking up ultrasound images is also provided in the region of the catheter tip 2, the supply and signal lines thereof likewise being conducted toward the outside in the catheter envelope 3.

Figure 2:
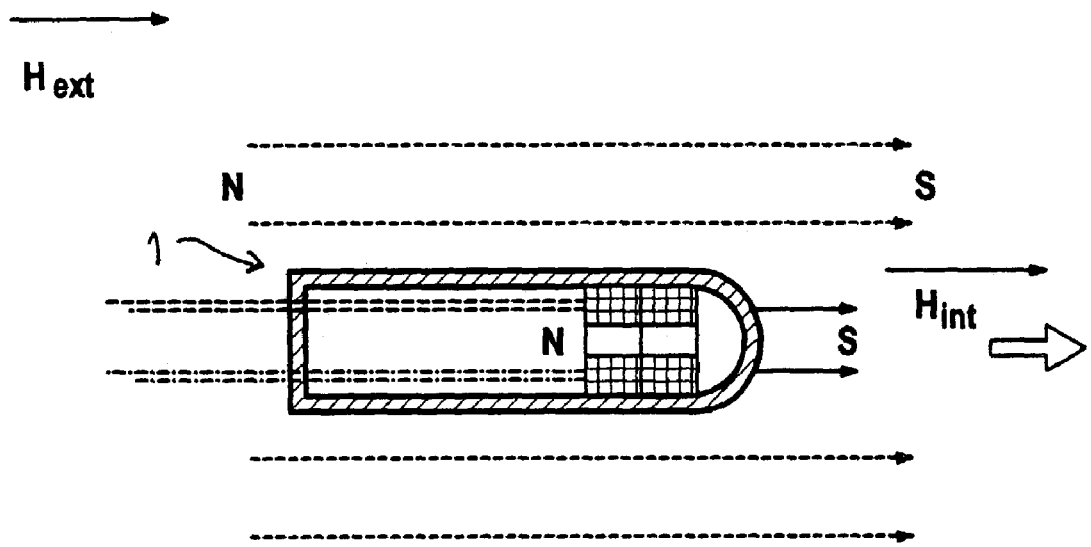
FIGS. 2-5 show the tip of the catheter from FIG. 1 in section, with respectively differently directed external and internal magnetic fields.
Figure 3:
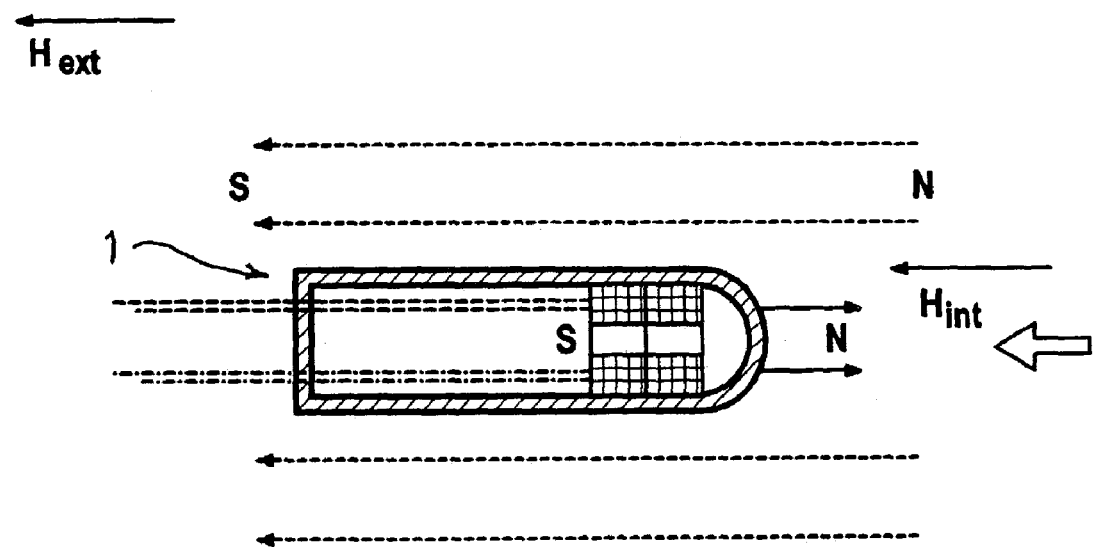

FIGS. 2 and 3 show the possibility of moving the catheter contact-free in the inside of the body using an external magnetic field that interacts with the magnetic field generated with the electromagnets 4. In FIG. 2, an external magnetic field $H_{ext}$ that resides horizontally in the illustrated example is generated with a magnetic field-generating device (not shown in detail). U.S. Pat. No. 6,148,823 describes such a device. The field direction is indicated by specifying the poles N and S as well as by the respective directional arrows. The two electromagnets 4 are driven in order to undertake a movement of the catheter in the field direction, with the direction of current being selected such that the internal field $H_{int}$ lies in essentially the same direction as the external field. The two poles N and S as well as the directional arrows are also indicated for the internal field $H_{int}$. When the external field moves, the internal field and thus the catheter follow it.

A movement in the opposite direction is shown in FIG. 3 in view of the field directions. The external field as well as the internal field are repolarized, i.e. they now lie in the opposite direction. The only thing required with respect to the repolarization of the internal field generated via the electromagnets 4 is to reverse the direction of the current, as a result the field direction then automatically changes.

Figure 4:
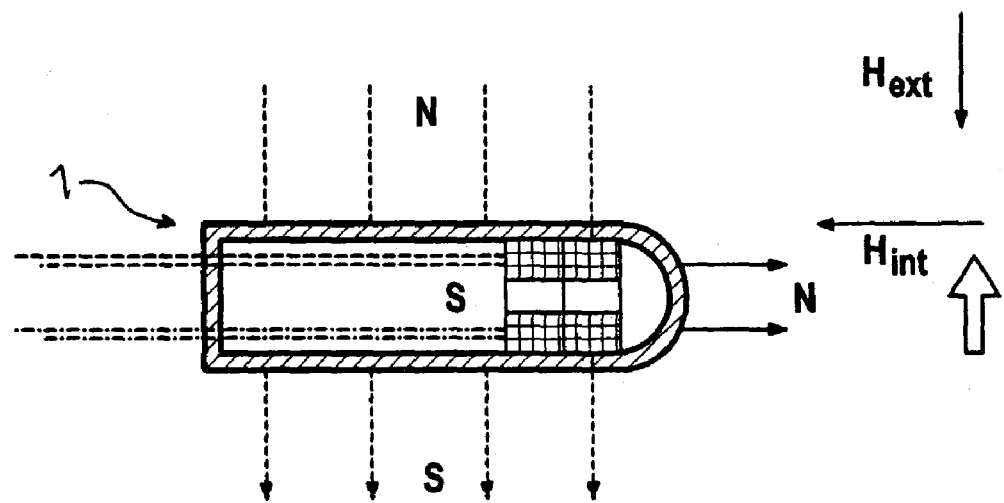
Figure 5:
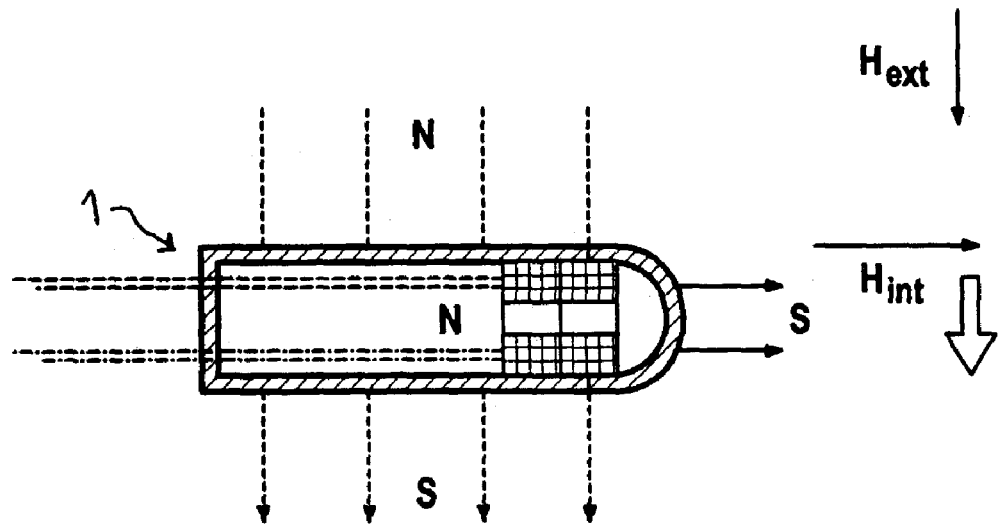

FIGS. 4 and 5 show the possibility of exerting an interaction force on the catheter tip directed essentially perpendicular to the longitudinal axis of the catheter as a result of the interaction of the external and the internal magnetic field. In FIG. 4, the external field is directed from top to bottom, residing vertically with respect to the longitudinal axis of the catheter. In the illustrated example, the internal field resides perpendicularly thereto and proceeds from right to left, i.e. the north pole lies at the right and the south pole lies at the left. Due to the interaction of the two fields, the catheter tip attempts to turn dependent on the direction of the internal magnetic field, i.e. upwardly in the illustrated example since the two fields would again be directed the same as a result of such a rotary motion. The internal field thus aligns according to the stronger external field.

The case is reversed in the example according to FIG. 5. Therein, the directions of the stronger external field and internal fields are reversed with respect to that shown in FIG. 4, so that a downward movement of the catheter tip 2 begins. Here as well, the internal field follows the external field.

As can be seen, thus, a tilting or rotary motion or a force that supports movement in the desired direction can be exerted on the catheter tip in a simple way. A corresponding field change of the inner field as well is merely required for this purpose. Of course, the interaction of the two fields can be improved and increased by intensifying the generated magnetic field by boosting the coil current, i.e. the field strength can likewise be set from the outside.

Figure 6:
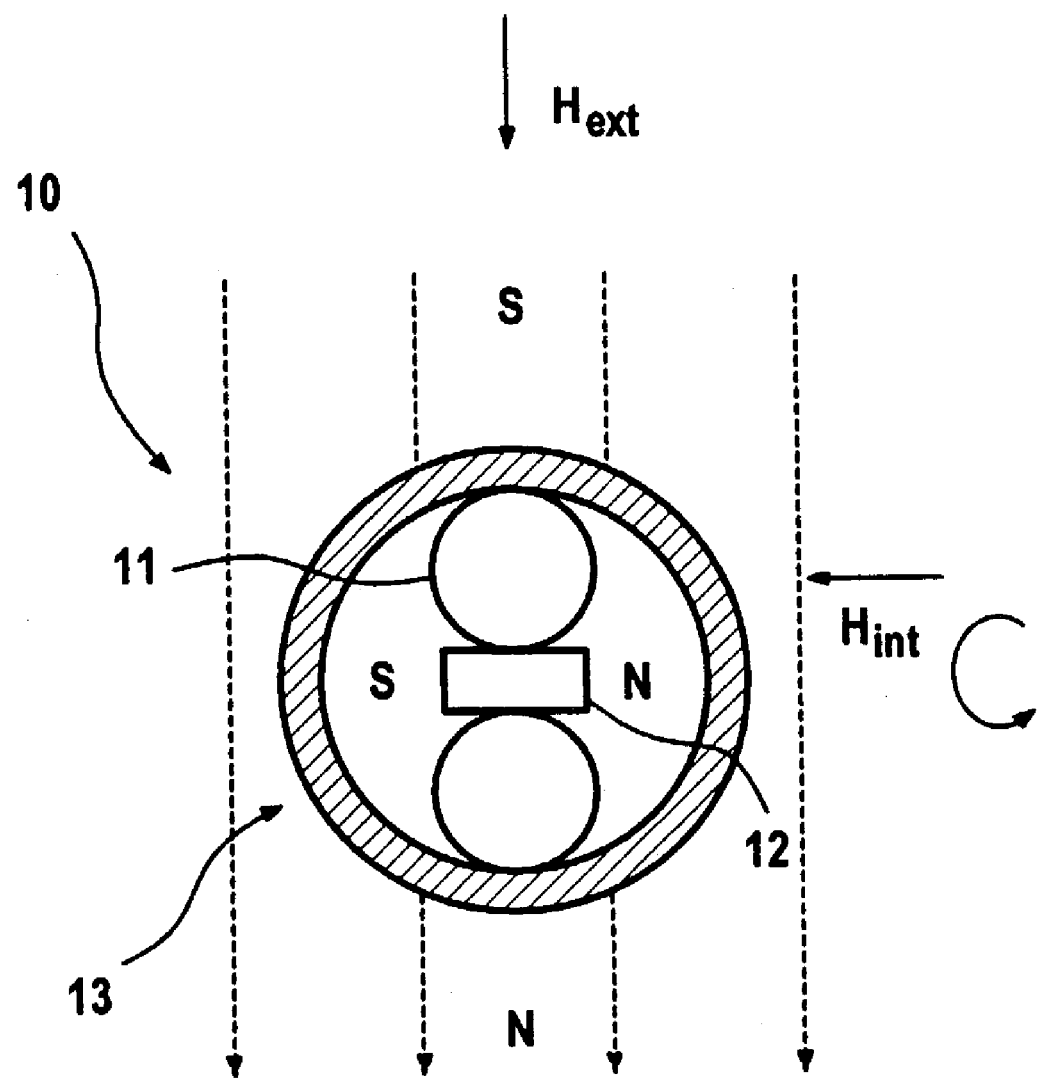
FIG. 6 is section through a second embodiment of the inventive catheter.

FIG. 6 shows a further embodiment of an inventive catheter 10 as a sectional view through the catheter tip. Here, the coil 11 and the coil core 12 of the electromagnet 13 lie in the catheter envelope such that the generated internal magnetic field lies essentially perpendicularly to the longitudinal catheter axis. In the illustrated example, the north pole N lies at the right and the south pole S lies at the left. Again, the field direction can be reversed by reversing the direction of the current through the coil 11.

When, as shown in FIG. 6, an external magnetic field is present that resides orthogonally relative to the internal magnetic field, then the internal magnetic field will also move in the direction of the external magnetic field, i.e. a rotation around the longitudinal catheter axis can be initiated. In the illustrated example, the catheter would turn toward the right around its axis, as indicated by the arrow, i.e. the "internal" south pole would turn toward the "external" north pole N and the "internal" north pole N would turn toward the "external" south pole S. The rotational principle known from a standard electric motor is utilized here, however, only a very short rotation is possible. In many instances, however, this short rotation suffices, i.e. when the catheter has become struck or the like.

Further, of course, it is conceivable to integrate, in a single catheter, electromagnets as shown at the catheter 1 as well as an electromagnet as described for the catheter 10, in order to utilize the different possibilities resulting from the positioning of the electromagnet. Moreover, a permanent magnet (not shown) can be present in the catheter tip, this likewise generating a magnetic field that, however, cannot be varied.

Although modifications and changes may be suggested by those skilled in the art, it is the intention of the inventor to embody within the patent warranted hereon all changes and modifications as reasonably and properly come within the scope of his contribution to the art.

I claim as my invention:

1. A catheter comprising:
   a catheter body configured for insertion in and movement through a living subject situated in a static magnetic field, said catheter body having a tip; and
   a magnetic field generator disposed at said tip that generates a variable magnetic field having a field strength and a field direction, said magnetic field generator comprising at least one electromagnet having a magnetic core and a coil with said coil having coil leads conducted through said catheter body and configured to proceed outside of the living subject to supply current to the coil from outside of said living subject that varies said magnetic field at said tip in at least one of said field strength and field direction to produce said movement of said catheter through said living subject exclusively by interaction of said magnetic field generated by said magnetic field generator with said static magnetic field.

2. A catheter as claimed in claim 1 wherein said catheter body is configured for intravascular insertion and movement in said living subject.

3. A catheter as claimed in claim 1 wherein said catheter body has a longitudinal axis, and wherein said at least one electromagnet generates said magnetic field substantially parallel to said longitudinal axis.

4. A catheter as claimed in claim 1 wherein said catheter body has a longitudinal axis, and wherein said at least one electromagnet generates said magnetic field substantially perpendicular to said longitudinal axis.

5. A catheter as claimed in claim 1 wherein said magnetic field generator comprises a plurality of electromagnets, each having a core and a coil, and each coil having leads conducted through said catheter body and configured to proceed outside of said living subject, for supplying current to each coil from outside of said living subject.

6. A catheter as claimed in claim 5 wherein said plurality of electromagnets are selectively operable individually and severally.

7. A catheter as claimed in claim 5 wherein said catheter body has a longitudinal axis, and wherein a first electromagnet in said plurality of electromagnets generates a first variable magnetic field substantially parallel to said longitudinal axis, and wherein a second electromagnet in said plurality of electromagnets generates a second variable magnetic field substantially perpendicular to said longitudinal axis.

8. A catheter as claimed in claim 1 further comprising a permanent magnet disposed at said catheter tip.

9. A catheter as claimed in claim 1 further comprising an ultrasound generating pick-up device disposed at said catheter tip, and having signal lines connected therethrough that are conducted through said catheter body and which are adapted to proceed to a location outside of said living subject.

10. A catheter as claimed in claim 1 wherein said core is comprised of iron.

* * * * *